United States Patent [19]

Hoe

[11] Patent Number: 5,522,887
[45] Date of Patent: Jun. 4, 1996

[54] EYE IMPLANT DEVICE AND METHOD

[76] Inventor: Michael J. V. Hoe, 3916 1st St., East Moline, Ill. 61244-3326

[21] Appl. No.: 394,678

[22] Filed: Feb. 24, 1995

[51] Int. Cl.⁶ .......................................... A61F 2/14
[52] U.S. Cl. ...................................... 623/4; 623/5
[58] Field of Search .................. 623/4, 5; 446/392, 446/389, 129

[56] References Cited

U.S. PATENT DOCUMENTS

| | | |
|---|---|---|
| 1,369,797 | 3/1921 | Fauer . |
| 2,571,721 | 10/1951 | Jardon . |
| 2,572,416 | 10/1951 | Wilson . |
| 2,617,994 | 11/1952 | Noelle . |
| 2,637,043 | 5/1993 | Morrel . |
| 2,688,139 | 9/1954 | Jardon . |
| 3,070,808 | 1/1963 | Allen . |
| 3,120,720 | 2/1964 | Brudney . |
| 3,228,741 | 1/1966 | Becker ......................................... 623/4 |
| 3,364,501 | 1/1968 | Stafford ......................................... 623/4 |
| 4,087,867 | 5/1978 | Hickman . |
| 4,629,442 | 12/1986 | Samo . |
| 4,737,132 | 4/1988 | Shunasku ............................ 446/392 X |
| 4,842,566 | 6/1989 | Nagao .................................. 446/392 X |
| 5,089,021 | 2/1992 | Vachet . |
| 5,330,529 | 7/1994 | Cepela . |

FOREIGN PATENT DOCUMENTS

| | | | |
|---|---|---|---|
| 633525 | 11/1978 | U.S.S.R. . | |
| 993937 | 2/1983 | U.S.S.R. .................................. 623/5 |

*Primary Examiner*—Mary Beth Jones
*Attorney, Agent, or Firm*—Rockey, Rifkin & Ryther

[57] ABSTRACT

A mechanism and method for filling the vacated eyesocket of a deceased person after an eyeball has been donated. A plurality of different sized implant members are positioned within each other, and the larger implant members can be opened to access the smaller implant members. Protrusions are formed on each implant member for engaging the inner surface of the deceased person's eyelids when the implant is positioned within the eyesocket. The different sized implants are also adapted for implantation within the deceased's eyeball when only the cornea and fluid sac have been removed during an in situ excision.

36 Claims, 1 Drawing Sheet

EYE IMPLANT DEVICE AND METHOD

BACKGROUND OF THE INVENTION

The invention relates to devices and methods for filling the space which has been vacated by the removal of an eyeball or portions thereof from a deceased person for purposes of scientific research or transplant to a living person.

Many persons elect to donate particular organs for scientific research or transplant upon death. Various parts of the human eye can be removed from a deceased persons body to benefit scientific research or to replace damaged or defective components of a living persons eye. In some states, the deceased person's entire eyeball is removed from the eyesocket by a technician authorized to perform such procedures. This procedure is known as an enucleation. In other states, the technician will perform what is referred to as an in situ excision, which is the removal of the cornea from the eyeball. The cornea is the clear covering over the colored portion at the front of the eyeball. In such a procedure the technician makes a circular incision a few millimeters outside of the perimeter of the cornea and peals off the cornea and leaves the rest of the eyeball in place within the eye socket. The cornea is then preserved in a solution for later transplant or scientific research.

After an in situ excision, an embalmer will typically remove the sac of fluid from the center of the eyeball which has been exposed by removal of the cornea. Removal of the fluid sac prevents the fluid from seeping out of the eye at a later time. The white portion of the eyeball which remains in the eyesocket is not rigid, and since it is no longer supported by the sac of fluid, the white portion of the eyeball will not retain its previous rounded shape but will generally collapse. A collapsed eyeball will make the deceased person's eyes look generally sunken and unnatural after the eyelids are closed. It is general practice for the embalmer to replace this fluid sac with embalming materials in order to support the collapsed eyeball and to thereby create a natural look when the eyelids of the deceased are closed. It is typical practice within the industry for the embalmer to fill the space within the eyeball with embalming clay, cotton or gauze. This process can be a relatively delicate task, and can therefore be relatively time consuming.

Out of respect for the deceased, it is the general practice within states that remove the entire eyeball from the deceased's eyesocket to fill the vacant space within the eyesocket. If the eyesocket is not filled after removal of the eyeball, the eyelid will appear sunken and unnatural. Therefore, filling the eyesocket also gives the deceased person's body a natural appearance. It is general practice within the industry to fill the vacated eyesocket with embalming clay, gauze or cotton. Typically the embalmer will wad up an amount of cotton or gauze and place it in the eyesocket, and then place clay within the eyesocket and form it to the general size and shape of the removed eyeball. Therefore the embalmer must mold the gauze or clay into the shape of an eyeball each time an eyeball is harvested. It is often difficult for the embalmer to replicate the shape of the removed eyeball, and the embalmer often spends an undesirably large amount of time working the clay or gauze into the shape and size of the removed eyeball. Once the gauze or clay has been properly shaped, the embalmer places a small cap over the clay and gauze. The cap has small upstanding spikes punched in it which serve to engage the inner surface of the eyelid for securely holding the eyelid in a closed position.

In the past, technicians have also replaced the removed eyeball with other structures such as a marble or a ball bearing. However, if the marble or ball bearing does not have the general size and shape of the removed eyeball, the deceased person will not have a natural look after implantation. Although the eyeballs of mature adult humans tend to be relatively similar in size and shape, some people have eyeballs which are slightly smaller or larger than the average. The human eyeball grows to its mature full size generally by the time the person reaches pre-pubescence at about the age of 11, and therefore it is common for young persons below the age of 11 to have eyeballs smaller than the average adult. If the marble or ball bearing which is used to fill the vacant eyesocket is too small, the technician must take the additional steps of inserting clay and gauze or cotton to further fill the eye socket. If the marble or ball bearing is too large it may not fit into the eyesocket or may yield an unnatural appearance. Therefore, a technician would be required to locate a ball bearing or marble which matches the particular size of the removed eyeball. Once the technician has properly filled the eyesocket with a ball bearing or marble, he then inserts the spiked cap in an attempt to hold the eyelids closed. But if the cap is placed directly against the marble or ball bearing the cap may slide around and not retain the eyelid in a closed position.

It would therefore be desirable to provide a method and mechanism which allows a technician to quickly and easily fill the space vacated by removal of the cornea, fluid sac or entire eyeball of a deceased. It would be desirable for such a mechanism to give the deceased a natural appearance. When an entire eyeball is removed from the deceased, it would be desirable to eliminate the need for an embalmer or technician to form a prosthetic eyeball out of gauze, clay or cotton each time an eyeball is harvested. It would be desirable for such a method and structure to result in the eyelid of the deceased being securely held in a closed position. It would also be desirable to provide a method and mechanism which is adapted to easily replace a variety of different sizes of eyeballs. It would also be desirable to provide a mechanism which allows an embalmer to more easily fill the space vacated at the center of an eyeball when the fluid sac has been removed after an in situ excision.

SUMMARY OF THE INVENTION

The preferred embodiment of the present invention provides an implant member having the general size and shape of a mature adult eyeball. A technician who has removed an entire eyeball from a deceased can quickly and easily place the implant in the eyesocket vacated by the donated eyeball, thereby eliminating the need to specially form clay and gauze by hand into the size and shape of the donated eyeball. Protrusion members are formed on the front portion of the implant member for engaging the inner surface of the deceased person's eyelid for securely holding the deceased person's eyelids in a closed position. The preferred embodiment provides an implant the size of an average adult eyeball, and two progressively smaller sized implant members which fit within the average sized implant. The average or largest implant and the medium sized implant are formed of plastic halves or shells which can be snapped apart to access the implant members positioned inside. The preferred embodiment therefore provides a mechanism which allows an embalmer to fill the space vacated by a variety of sizes of eyeballs quickly and easily.

The present invention is also adapted to fill the space vacated by the fluid sac removed from a deceased's eyeball after a technician has removed the cornea via an in situ excision. The proper sized implant can be positioned within the eyeball for supporting the remaining white portion of the eyeball to yield a natural look when the eyelids are closed. The spiked protrusions will engage the inner surfaces of the eyelids to maintain the eyelids in a closed position.

The implant members according to the present invention can be provided to technicians in the kits having the supplies needed to carry out the removal procedure. Therefore the implants according to the present invention are available for use by the embalmer directly after the removal procedure.

DESCRIPTION OF THE PREFERRED EMBODIMENT

Figure 1:
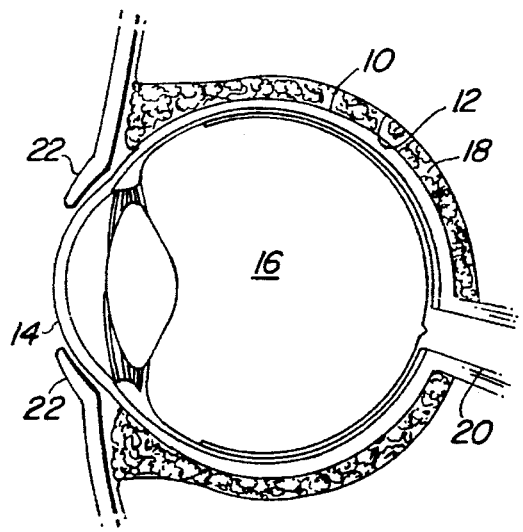
FIG. 1 is a cross sectional view of a mature adult human's eyeball within the eyesocket.

Referring now to FIG. 1, there is shown a cross sectional view of an adult human eyeball 10 within an eyesocket 12. The cornea 14 is the colored portion of the persons eye located at the front of the eyeball 10. A fluid sac 16 is positioned within the eyeball 10 and helps give the eyeball 10 its shape. The eyesocket 12 is formed of bone material. A layer of fatty tissue 18 is positioned between the eyeball 10 and the eyesocket 12. Muscles (not shown) as well as the optic nerve 20 are attached to the eyeball 10 and must be cut in order to remove the eyeball 10 from the socket 12. Eyelids 22 are also shown in FIG. 1.

Figure 2:
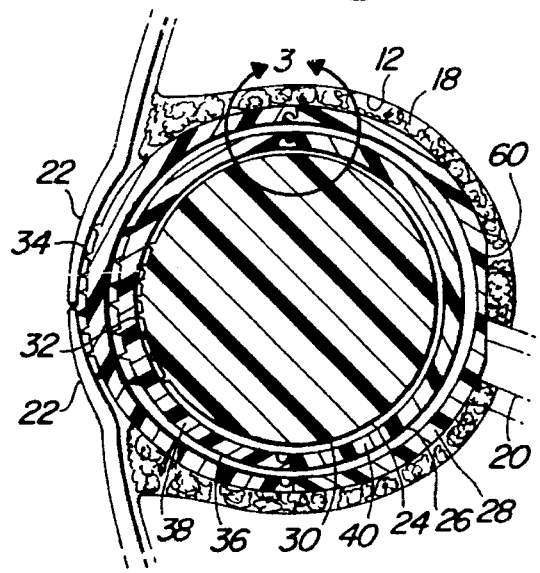
FIG. 2 is a cross sectional view of the implant members according to the preferred embodiment of the present invention and positioned within an eyesocket after an eyeball has been removed in an enucleation procedure.
Figure 5:
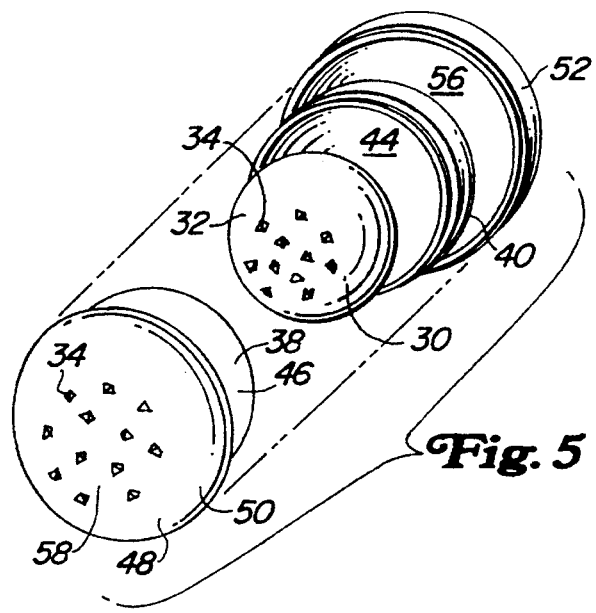
FIG. 5 is an exploded view of implant members according to the preferred embodiment of the present invention.
Figure 4:
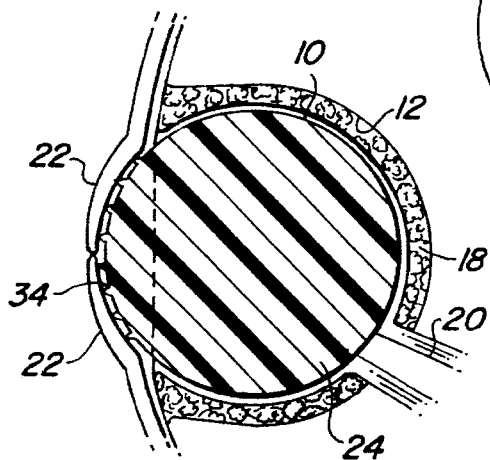
FIG. 4 is a cross sectional view of an implant member according to the present invention in place within an eyeball of a deceased after an in situ excision has been performed.

Referring now to FIG. 2, there is shown the preferred embodiment positioned within a human eyesocket 12 according to the present invention. First, second and third implant members 24, 26 and 28 are provided by the present invention, as seen in FIGS. 2 and 5. The first implant member 24 according to the preferred embodiment has an outer surface 30 of a size and shape generally smaller that an average mature adult's eyeball. The first implant member 24 according to the preferred embodiment is approximately 18 millimeters from front to back and approximately 17 millimeters from top to bottom. The front portion 32 of the outer surface 30 includes spikes or protrusions 34 which extend outwardly from the outer surface 30. The first implant member 24 is formed of plastic and is solid in order to reduce manufacturing costs.

Figure 3:
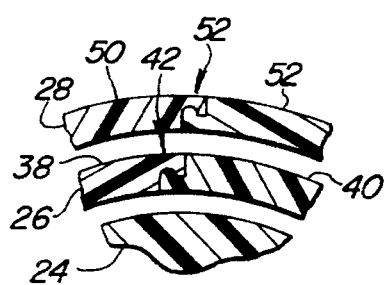
FIG. 3 is a sectional view of the mating features of the shell members according to the preferred embodiment of the present invention.

The present invention includes a second or intermediate sized implant member 26 having an outer surface 36 which is also generally smaller in size and shape than an average mature adult eyeball. The second implant member 26 is approximately 21 millimeters from front to back, and is approximately 20 millimeters from top to bottom. The second implant member 26 has first and second portions or halves 38 and 40 which releasably fit together. Mating portions 42, as best seen in FIG. 3, are formed in the first and second portions 38 and 40 which allow them to be easily snapped together or detached from one another. The embodiment shown in the drawings is a snap fit, but other mating features such as a friction fit or a threaded feature could also be utilized. The first and second shell portions 38 and 40 define a hollow inner portion 44 which has an inner diameter large enough to receive the first implant member 24. Protrusions 34 are formed in the front portion 46 of the second implant member 26 for engaging the inner surface of the deceased person's eyelids 22 for maintaining the eyelids 22 in a closed position.

The present invention also provides a third or average sized implant member 28 which has an outer surface 48 generally similar in size to that of an average mature adult eyeball. The third implant member 28 according to the preferred embodiment is approximately 24 millimeters from front to back, and is approximately 23 millimeters from top to bottom. First and second shell portions or halves 50 and 52 releasably snap together to define the third implant member 28. Mating features 54, as best seen in FIG. 3, formed in the first and second portions 50 and 52 allow the two shells 50 and 52 to easily snap together or apart. An interference or snap fit is shown, but other mating features such as a friction fit or threaded features could be utilized. The shells 50 and 52 form an inner hollow portion 56 having an inner diameter large enough to receive the second implant member 26. Protrusion members or spikes 34 are formed in the front portion 58 of the third implant member 28 which secure the deceased person's eyelids 22 in a closed position. The third implant member 28 also includes a flatted portion 60 which allows an embalmer to place it on a flat surface without it rolling out of place.

Next, the operation and use of the preferred embodiment according to the present invention will be discussed. According to the preferred embodiment, the first implant member 24 is positioned within the second implant member 26, and the second implant member 26 is positioned within the third implant member 28. Therefore the present invention provides a plurality of different sized eye implants in a compact configuration. The first, second and third implant members can be made from rubber material. The assembled eye implants 24 26 and 28 can be included as part of the kit of materials and supplies the technician would receive from an eye bank or other organization before an enucleation or in situ excision is to be performed. The embalmer or technician can then use the present invention once the technician has completed the removal procedure.

If the entire eyeball 10 has been removed by the technician during an enucleation, and the eyeball 10 was the size of an average adult eyeball, then the technician or embalmer would simply place the third implant member 28 into the empty eyesocket 12 and close the deceased person's eyelids 22. The first and second implant members 24 and 26 would remain within the third implant member 28, thereby minimizing the effort on the part of the embalmer. The protrusions 34 located on the front portion 58 of the third implant member 28 engage the inner surface of the eyelids 22 for keeping the eyelids 22 closed.

If the donated eyeball 10 is smaller than an average adult's eyeball then the embalmer would open the third implant member 28 and remove the second implant member 26. If the removed eyeball 10 was the approximate size of the second implant member 26, then the embalmer can place the second implant member 26 in the empty eye socket 12 and close the eyelids 22. The first implant 24 remains within the second implant 26, and the third implant member 28 can be discarded. If the removed eyeball 10 is smaller than the second implant 26, then the embalmer can snap open the second implant member 26 and place the first implant member 24 in the eyesocket 12. The second and third implant members 26 and 28 can then be discarded. The protrusions 34 on the front portion of the implant members will engage the inner portion of the eyelids 22 for keeping the eyelids closed.

If the removed eye is larger than the average adult eyeball, then the third implant member 28 can be placed in the eyesocket 12 and a standard eye cap having spikes as discussed above in the Background of the Invention can be placed over the protrusions 34 at the front 58 of the third implant member 28. This will increase the effective size of the structure placed within the eyesocket 12 to better replicate the larger size of the removed eyeball. The cap will be securely held in place and prevented from slipping by the spikes 34 formed on the front portion 58 of the third implant member 28.

The present invention has been described above as having three different sizes of implants 24, 26 and 28 which are situated within one another. However, less than or more than three implants could be provided within the spirit of the present invention. Furthermore, the present invention is described above as having the largest implant member 28 of a size generally similar to an average adult's eyeball, but the largest implant member could also be sized larger than an average adult's eyeball. An implant member having the size of an average adult's eyeball could then be provided as one of the smaller sized implant members.

The preferred embodiment of the present invention allows the embalmer or technician to quickly and easily fill the empty eyesocket with a structure that generally replicates the shape and size of the donated eyeball. The present invention eliminates the time consuming process of forming gauze or clay by hand into the shape and size of the donated eyeball 10. Since the protrusions 34 are formed directly on the outer surface of the implant members 24, 26 and 28, the additional step of inserting a separate spiked cap is eliminated. Furthermore, the preferred embodiment provides a plurality of different sizes which can be inserted into the empty eyesocket 12, and therefore the embalmer is not required to search for a marble or ball bearing that would match the size of the donated eye 10.

The present invention is also adapted for use after an in situ excision has been performed. Once the cornea 14 has been cut and peeled away, and the fluid sac 16 has been removed, the embalmer can insert the proper sized implant member 24, 26 or 28 into the eyeball 10. The implant member 24, 26 or 28 would thereby support the white portion of the eyeball 10 in the absence of the fluid sac 16. If a cornea 14 and fluid sac 16 is removed from an average sized adult eyeball, then the embalmer can snap open the third implant member 28 and remove the second implant member 26. The second implant member 26 is generally the size of the cavity within the empty eyeball 10. The embalmer can squeeze the second implant member 26 slightly while holding open the empty eyeball 10 and insert the second implant member 26 through the opening created by the excised cornea 14. The embalmer could also make a small incision into the eyeball 10 at the edge of the opening left by the removed cornea 14 and thereby facilitate inserting the second implant member 26 into the eyeball 10. The embalmer can utilize whichever implant member 24, 26 or 28 has a size closest to the size of the cavity within the eyeball 10.

The present invention therefore serves the dual purpose of helping an embalmer fill the space vacated by a technician when either the cornea 14 is removed during an in situ excision or when the entire eyeball 10 is removed during an enucleation procedure. The present invention could therefore be included in the kit of supplies typically sent to all technicians regardless of which procedure is to be performed.

I claim:

1. A mechanism, comprising:

first and second shell members which fit together to define a shape and size generally similar to that of an eyeball removed from an eye socket of a deceased person, said first shell member having protrusion means for engaging the inner surface of an eyelid of said deceased person for retaining the eyelid in a closed position when said shell members are positioned within said eyesocket and further comprising another implant member enclosed within said first and second shell members and adapted for insertion into the eyesocket of the deceased when the eyeball removed from said deceased is relatively small.

2. The invention of claim 1, wherein said first and second shell members have mating portions which generally snap together for rigidly coupling the first and second shells to each other.

3. The invention of claim 2, wherein said first and second shell members fit together to define an implant member having front, back, top and bottom portions, said implant member being approximately 24 millimeters from the front to the back portions, and being approximately 23 millimeters from the top to the bottom portion.

4. The invention of claim 1, wherein said implant member which is enclosed within the first and second shell members is adapted for insertion into the eyeball of a deceased after a cornea and fluid sac have been removed from said deceased.

5. A mechanism adapted for replacing an eyeball removed from a deceased person's eyesocket, comprising:

a pair of implant members, one of the implant members having an outer surface which is the general size and shape of an average mature adult eyeball, the other implant member having an outer surface which has a general size and shape smaller than an average mature adult eyeball, each of said implant members having protruding members for engaging an inner surface of said deceased person's eyelid for maintaining said eyelid in a closed position when the implant is positioned within the eyesocket, said average sized implant member having first and second portions releasably coupled together to define the outer surface of the average sized implant member, said first and second portions defining a generally hollow inner portion within which said smaller than average sized implant member is positioned.

6. The invention of claim 5, wherein said smaller than average implant member has a front to back dimension of approximately 18 millimeters, and a top to bottom dimension of approximately 17 millimeters.

7. The invention of claim 5, wherein said average sized implant member has a front to back dimension of approximately 24 millimeters, and a top to bottom dimension of approximately 23 millimeters.

8. The invention of claim 5, wherein said smaller than average sized implant member has a front to back dimension of approximately 18 millimeters, and a top to bottom dimension of approximately 17 millimeters, and said average sized implant member has a front to back dimension of approximately 24 millimeters, and a top to bottom dimension of approximately 23 millimeters.

9. The invention of claim 5, and further comprising:

an intermediate sized implant member having an outer surface of a size and shape smaller than the average sized implant member and larger than the smaller than average sized implant member, said intermediate sized implant member having first and second portions releasably coupled together to define a generally hollow inner portion within which the smaller than average sized implant member is positioned, said intermediate sized implant member being positioned within the hollow inner portion of the average sized implant member, and having protruding members for engaging an inner surface of a deceased person's eyelid for maintaining said eyelid in a closed position when the intermediate sized implant member is removed from the inner portion of the average sized implant member and inserted into the deceased's eyesocket in place of the removed eyeball.

10. The invention of claim 9, and further comprising mating portions formed between the first and second portions of the average sized and intermediate sized implant members for allowing the respective first and second portions to be releasably coupled together.

11. The invention of claim 10, wherein said average sized and intermediate sized implant members are a plastic material.

12. The invention of claim 10, wherein said average sized and intermediate sized implant members are a rubber material.

13. The invention of claim 9, and further comprising mating portions of an interference type formed between the first and second portions of the average sized and intermediate sized implant members for allowing the respective first and second portions to be releasably snapped together and apart from each other.

14. The invention of claim 9, wherein said smaller than average sized implant member is a generally solid mass of plastic material.

15. The invention of claim 9, wherein said intermediate sized implant member has a front to back dimension of approximately 21 millimeters, and a top to bottom dimension of approximately 20 millimeters.

16. The invention of claim 9, wherein said smaller than average sized implant member has a front to back dimension of approximately 18 millimeters, and a top to bottom dimension of approximately 17 millimeters, said intermediate sized implant member has a front to back dimension of approximately 21 millimeters, and a top to bottom dimension of approximately 20 millimeters, and said average sized implant member has a front to back dimension of approximately 24 millimeters, and a top to bottom dimension of approximately 23 millimeters.

17. The invention of claim 16, wherein said smaller than average sized implant member is positioned within an eyeball of a deceased after a cornea and fluid sac have been removed from the eyeball of the deceased.

18. The invention of claim 16, wherein said intermediate sized implant member is positioned within an eyeball of a deceased after a cornea and fluid sac have been removed from the eyeball of the deceased.

19. The invention of claim 9, wherein said intermediate sized implant member is positioned within an eyeball of a deceased after a cornea and fluid sac have been removed from the eyeball of the deceased.

20. The invention of claim 9, wherein said smaller than average sized implant member is a generally solid mass of rubber material.

21. The invention of claim 5, wherein said average sized and smaller than average sized implant members are a plastic material.

22. The invention of claim 5, wherein said smaller than average sized implant member is a generally solid mass of plastic material.

23. The invention of claim 5, wherein said smaller than average sized implant member is positioned within an eyeball of a deceased after a cornea and fluid sac have been removed from the eyeball of the deceased.

24. The invention of claim 5, wherein said average sized and smaller than average sized implant members are a rubber material.

25. The invention of claim 5, wherein said smaller than average sized implant member is a generally solid mass of rubber material.

26. A mechanism adapted for filling the space vacated within an eyeball of a deceased after a cornea and fluid sac have been removed from an eyeball during an in situ procedure, comprising:

first and second implant members, each of said implant members having protruding members for engaging an inner surface of said deceased person's eyelid for maintaining said eyelid in a closed position when the implant is positioned within the eyeball, said second implant member having first and second portions releasably coupled together to define the outer surface of the second implant member, said first and second portions defining a generally hollow inner portion within which said first implant member is positioned, said second implant member being openable for allowing the first implant member to be removed from the hollow inner portion for placement within an eyeball of a deceased after a cornea and fluid sac have been removed from the eyeball during an in situ procedure and when said first implant member generally matches the size and shape of the cavity in the eyeball, and said second implant member is positionable within an eyeball of a deceased after a cornea and fluid sac have been removed from the eyeball during an in situ procedure and when said second implant member generally matches the size and shape of the cavity in the eyeball.

27. The invention of claim 26, wherein said first implant member has a front to back dimension of approximately 18 millimeters, and a top to bottom dimension of approximately 17 millimeters.

28. The invention of claim 26, wherein said second implant member has a front to back dimension of approximately 21 millimeters, and a top to bottom dimension of approximately 20 millimeters.

29. The invention of claim 26, wherein said first implant member has a front to back dimension of approximately 18 millimeters, and a top to bottom dimension of approximately 17 millimeters, and the second implant member has a front to back dimension of approximately 21 millimeters, and a top to bottom dimension of approximately 20 millimeters.

30. The invention of claim 26, and further including a third implant member having first and second portions releasably coupled together to define a generally hollow inner portion within which the second implant member is positioned, said third implant member having protrusions for engaging an inner surface of an eyelid when positioned within an eyeball, said third implant member being positionable within an eyeball of a deceased after a cornea and fluid sac of a deceased's eyeball has been removed during an in situ excision and when said third implant member is the general size and shape of the cavity which remains after removal of the fluid sac, said first and second portions of the third implant member being openable for exposing the second implant member for implantation within an eyeball.

31. The invention of claim 30, wherein said first implant member has a front to back dimension of approximately 18 millimeters, and a top to bottom dimension of approximately 17 millimeters.

32. The invention of claim 30, wherein said second implant member has a front to back dimension of approximately 21 millimeters, and a top to bottom dimension of approximately 20 millimeters.

33. The invention of claim 30, wherein said third implant member has a front to back dimension of approximately 24 millimeters, and a top to bottom dimension of approximately 23 millimeters.

34. The invention of claim 30, wherein said first implant member has a front to back dimension of approximately 18 millimeters, and a top to bottom dimension of approximately 17 millimeters, and the second implant member has a front to back dimension of approximately 21 millimeters, and a top to bottom dimension of approximately 20 millimeters.

35. The invention of claim 30, wherein said first implant member has a front to back dimension of approximately 18 millimeters, and a top to bottom dimension of approximately 17 millimeters, and the second implant member has a front to back dimension of approximately 21 millimeters, and a top to bottom dimension of approximately 20 millimeters, and said third implant member has a front to back dimension of approximately 24 millimeters, and a top to bottom dimension of approximately 23 millimeters.

36. The invention of claim 30, wherein said first and second portions of the second and third implant members further include mating portions which allow the respective first and second portions to be releasably coupled together.

* * * * *

UNITED STATES PATENT AND TRADEMARK OFFICE
CERTIFICATE OF CORRECTION

PATENT NO. : 5,522,887                               Page 1 of 6
DATED      : June 4, 1996
INVENTOR(S): Michael J. Van Hoe It is certified that error appears in the above-indentified patent and that said Letters Patent is hereby corrected as shown below:

Item [19] of cover page, line 2, delete "Hoe" and insert therefor
--Van Hoe--.

Item [76] of cover page, line 1, delete "V. Hoe" and insert therefor
--Van Hoe--.

Column 6, Claim 5, line 37, delete "one" and insert therefor --a first--.
          line 37, after "the" insert --pair of--

Column 6, Claim 5, line 39, delete "the other" and insert therefor --a second of the pair of--.

Column 6, Claim 5, line 40, delete "member" and insert therefor
--members--.

Column 6, Claim 5, line 46, delete "average sized" and insert therefor
--first--.

Column 6, Claim 5, line 49, delete "average sized" and insert therefor
--first--.

Column 6, Claim 5, line 51, delete "smaller than average sized" and insert therefor --second--.

UNITED STATES PATENT AND TRADEMARK OFFICE
CERTIFICATE OF CORRECTION

PATENT NO. : 5,522,887
DATED : June 4, 1996
INVENTOR(S) : Michael J. Van Hoe

It is certified that error appears in the above-indentified patent and that said Letters Patent is hereby corrected as shown below:

Column 6, Claim 6, lines 53-54, delete "smaller than average" and insert therefor --second--.

Column 6, Claim 7, line 57, delete "average sized" and insert therefor --first--.

Column 6, Claim 8, lines 61-62, delete "smaller than average sized" and insert therefor --second--.

Column 6, Claim 8, line 65, delete "average sized" and insert therefor --first--.

Column 7, Claim 9, line 2, delete "an intermediate" and insert therefor --a third intermediate--.

Column 7, Claim 9, lines 3-4, delete "average sized" and insert therefor --first--.

Column 7, Claim 9, lines 4-5, delete "smaller than average sized" and insert therefor --second--.

Column 7, Claim 9, line 5, after "said" insert --third--.

UNITED STATES PATENT AND TRADEMARK OFFICE
CERTIFICATE OF CORRECTION

PATENT NO. : 5,522,887
DATED : June 4, 1996
INVENTOR(S) : Michael J. Van Hoe

It is certified that error appears in the above-indentified patent and that said Letters Patent is hereby corrected as shown below:

Column 7, Claim 9, lines 8-9, delete "smaller than average sized" and insert therefor --second--.

Column 7, Claim 9, line 9, after "said" insert --third--.

Column 7, Claim 9, line 11, delete "average sized" and insert therefor --first--.

Column 7, Claim 9, line 14, after "the" insert --third--.

Column 7, Claim 10, line 21, delete "average sized" and insert therefor --first--.

Column 7, Claim 10, line 21, after "and" insert therefor --third--.

Column 7, Claim 11, line 24, delete "average sized" and insert therefor --first--.

Column 7, Claim 11, line 25, after "and" insert --third--.

Column 7, Claim 12, line 27, delete "average sized" and insert therefor --first--.

Column 7, Claim 12, line 28, after "and" insert --third--.

UNITED STATES PATENT AND TRADEMARK OFFICE
CERTIFICATE OF CORRECTION

PATENT NO. : 5,522,887
DATED : June 4, 1996
INVENTOR(S) : Michael J. Van Hoe

It is certified that error appears in the above-indentified patent and that said Letters Patent is hereby corrected as shown below:

Column 7, Claim 13, line 32, delete "average sized" and insert therefor --first--.

Column 7, Claim 13, line 32, delete "and intermediate" and insert therefor --and third intermediate--.

Column 7, Claim 14, lines 36-37, delete "smaller than average sized" and insert therefor --second--.

Column 7, Claim 15, line 39, after "said" insert --third--.

Column 7, Claim 16, lines 43-44, delete "smaller than average sized" and insert --second--.

Column 7, Claim 16, line 47, after "said" insert --third--.

Column 7, Claim 16, line 51, delete "average sized" and insert therefor --first--.

Column 7, Claim 17, lines 54-55, delete "smaller than average sized" and insert therefor --second--.

Column 7, Claim 18, line 58, after "said" insert --third--.

UNITED STATES PATENT AND TRADEMARK OFFICE
CERTIFICATE OF CORRECTION

PATENT NO. : 5,522,887
DATED : June 4, 1996
INVENTOR(S) : Michael J. Van Hoe

It is certified that error appears in the above-indentified patent and that said Letters Patent is hereby corrected as shown below:

Column 7, Claim 19, line 62, after "said" insert --third--.

Column 7, Claim 20, lines 66-67, delete "smaller than average sized" and insert therefor --second--.

Column 8, Claim 21, line 1, delete "average sized" and insert therefor --first--.

Column 8, Claim 21, line 2, delete "smaller than average sized" and insert therefor --second--.

Column 8, Claim 22, lines 4-5, delete "smaller than average sized" and insert therefor --second--.

Column 8, Claim 23, lines 7-8, delete "smaller than average sized" and insert therefor --second--.

Column 8, Claim 24, line 11, delete "average sized" and insert therefor --first--.

Column 8, Claim 24, line 12, delete "smaller than average sized" and insert therefor --second--.

UNITED STATES PATENT AND TRADEMARK OFFICE
CERTIFICATE OF CORRECTION

PATENT NO.  : 5,522,887
DATED       : June 4, 1996
INVENTOR(S) : Michael J. Van Hoe It is certified that error appears in the above-indentified patent and that said Letters Patent is hereby corrected as shown below:

Column 8, Claim 25, lines 14-15, delete "smaller than average sized" and insert --second--.

Signed and Sealed this

Fifth Day of November, 1996

BRUCE LEHMAN

*Attest:*

*Attesting Officer*    *Commissioner of Patents and Trademarks*